United States Patent [19]

Tice

[11] Patent Number: 4,517,851
[45] Date of Patent: May 21, 1985

[54] SYSTEM FOR CONTROLLING SEPTUM DAMAGE

[75] Inventor: Gregory Tice, Lutherville, Md.

[73] Assignee: Becton Dickinson and Company, Paramus, N.J.

[21] Appl. No.: 496,716

[22] Filed: May 20, 1983

[51] Int. Cl.³ ............................................ G01N 35/00
[52] U.S. Cl. ............................. 73/864.91; 73/864.86; 141/130; 141/165; 141/329; 422/64; 422/102; 422/104
[58] Field of Search ...................... 422/64, 63, 65, 102, 422/103, 104; 73/864.87, 864.86, 864.91, 864.85, 864.82; 141/165, 130, 312, 329, 330, 19

[56] References Cited

U.S. PATENT DOCUMENTS

| | | | |
|---|---|---|---|
| 3,549,330 | 12/1970 | Jungner et al. | 422/64 |
| 3,550,453 | 12/1970 | Lightner et al. | 73/864.87 X |
| 3,676,679 | 7/1972 | Waters | 250/380 |
| 3,680,967 | 8/1972 | Engelhardt | 73/864.91 X |
| 3,897,216 | 7/1975 | Jones | 422/65 X |
| 3,918,920 | 11/1975 | Barber | 422/104 |
| 3,964,867 | 6/1976 | Berry | 422/64 X |
| 4,150,673 | 4/1979 | Watt | 141/329 X |
| 4,170,625 | 10/1979 | Welch | 422/64 |
| 4,224,278 | 9/1980 | Hogen Esch | 422/63 X |
| 4,359,447 | 11/1982 | Welch | 422/64 X |

FOREIGN PATENT DOCUMENTS

| | | | |
|---|---|---|---|
| 950703 | 7/1974 | Canada | 422/65 |
| 51288 | 5/1982 | European Pat. Off. | 422/102 |
| 1250479 | 12/1960 | France | 141/329 |
| 503637 | 12/1954 | Italy | 422/64 |
| WO83/00102 | 1/1983 | PCT Int'l Appl. | 422/102 |
| 1192009 | 5/1970 | United Kingdom | 422/64 |

OTHER PUBLICATIONS

"Removable Septum Port for a Mass Spectrometer All-Glass Inlet System", p. 216, *Analytical Chemistry*, vol. 49, No. 1, Jan. 1973, Walter G. Dunn et al.

Primary Examiner—S. Clement Swisher
Assistant Examiner—Tom Noland
Attorney, Agent, or Firm—James R. McBride

[57] ABSTRACT

The present invention is directed to a system for locating a vial in a predetermined location with respect to a needle which is used to penetrate a septum in the vial. The system includes a vial carrier having a well for receiving a vial. A penetrable septum is disposed in an opening in the vial. At least one needle penetrates the septum at periodic intervals. Locating means are provided within the vial carrier for establishing a predetermined location of the vial in relation to the needle. The locating means includes a plurality of contact points and urging means for establishing contact between the contact points and the locating surface. The urging means presses substantially on one side of the vial, which side is substantially opposite the locating means.

30 Claims, 4 Drawing Figures

SYSTEM FOR CONTROLLING SEPTUM DAMAGE

FIELD OF THE INVENTION

The present invention relates generally to a system for locating a vial with a penetrable septum in a predetermined position with respect to a plurality of needles which penetrate the septum at periodic intervals.

DESCRIPTION OF THE PRIOR ART

In commercial equipment which requires penetration of a septum, such as for gas chromatography, it is customary to introduce a sample of gas or liquid through the septum by injecting the sample through a hollow needle which penetrates the elastomeric septum. To prevent septum damage from causing leakage after a few tests, a guide is used which locates the needle in a position to enter the septum very nearly at the center of the circular septum. The result is that on each test after the first, the needle re-enters the cut or tear made by the needle on the first test and produces little additional damage. Thus, a great many tests can be made using a single septum, even though the needle is inserted manually.

Other commercial automated equipment requiring repetitive entry through a septum utilizes two or more hollow needles. An example of such type of commercial instrument is described in U.S. Pat. No. 3,676,679 to Waters. Such systems require repeated tests of the contents of a vial through the use of a plurality of hollow needles, usually two, to penetrate an elastomeric septum sealing the vial. The use of two needles permits a large volume of sample to be withdrawn rapidly and with controlled dilution but without any permanent reduction of pressure within the vial. Such vials may be under a slight positive pressure due to the growth of microrganisms. While one needle withdraws gas for analysis, the second needle admits gas to replace that withdrawn, restoring approximately the original pressure.

At each penetration, each needle produces a small cut or tear in the septum. Accidental rotation of the vial between successive tests soon produces an uncontrolled distribution of spetum damage. Since more than one needle is being used, it is not possible to provide a needle guide for insertion of the needle at the approximate center of the septum. The result is that when adjacent locations of septum damage happen to overlap, or to be too closely spaced, the functionality of the septum is destroyed. This limits the number of tests which can be made before septum failure is likely to occur. Furthermore, no definite number of tests can be made without loss of septum efficiency and it is possible that the septum will be destroyed prior to a single passage through automated testing equipment which requires repeated testings of a vial during the passage.

SUMMARY

The present invention provides a system for locating a vial with a penetrable septum in a predetermined position with respect to at least one needle which penetrate the septum at periodic intervals.

In general, the system includes a vial carrier containing a well, a vial having a cross sectional shape which permits insertion in the well, and locating means within the vial carrier for establishing a predetermined location for the vial in relation to at least one, and usually a plurality of needle(s) which penetrate a septum in the vial at periodic intervals. The locating means includes a plurality of contact points and urging means for establishing contact between the contact points and a locating surface.

For purposes of discussion, a vial is generally considered to include a body portion (which in most prior art applications is cylindrical) an opening in the top of the vial, a septum located in the opening and a seal surrounding the septum and the opening. The portion of the vial which consists of a gradual reduction in cross section to form a neck containing the opening is generally referred to as the finish of the vial.

DETAILED DESCRIPTION OF THE INVENTION

The system of the present invention is adapted for use with prior art automated equipment wherein a test head captures the finish of a vial and holds it in a definite location with respect to needles which penetrate the septum. Thus, if rotation of the vial is prevented between successive penetrations of the septum, the needles will penetrate the septum in the same position as the last penetration. Of course, if the needles are changed between successive penetrations of the septum, the new needles must be positioned in the same location as the previous set of needles to permit penetration of the septum in the same position.

In a preferred embodiment of the present invention, the body of the vial has a cross sectional shape which is such that it fits into a vial carrier in such a manner as to prevent rotation of the vial about a vertical axis. Each needle in the needle set is then constrained to enter the septum at a definite location and will do so on repeated penetrations of the septum.

In a system where the vial remains in the same vial carrier throughout all testing, the cross section of the vial might, for example, be in the shape of a circle, an equilateral triangle, an isosceles triangle, an irregular triangle or an isosceles trapezoid. A spring or other elastomeric object is used to press against one side of the vial to restrain the vial in a fixed predetermined position within the vial carrier.

In some situations, it is preferred to use a system in which the vial can be placed in the vial carrier only in a unique orientation. For example, a vial in the shape of an equilateral triangle could be replaced incorrectly if the vial was removed between tests. In addition, the vial might carry a machine readable label which would need to be in a particular location to be read. For these occasions, the body of the vial would preferably have an irregular shape, such as the cross sectional shape of an isosceles triangle or an isosceles trapezoid. The well in the vial carrier would be of a similar shape only a little larger so that the vial could be inserted only in a matching orientation. The vial would be urged by a spring into one vertex of the opening to prevent the vial from rotating about a vertical axis. In practice, it is possible to provide the vial with any irregular shape and the well of the vial carrier with a matching irregular shape.

Figure 1:
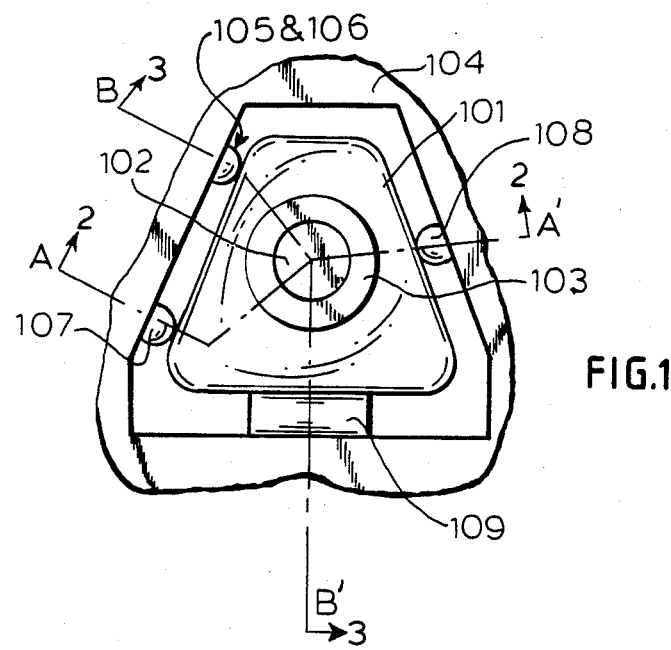
FIG. 1 is a top plan view of a vial located in a vial carrier in accordance with the invention.
Figure 2:
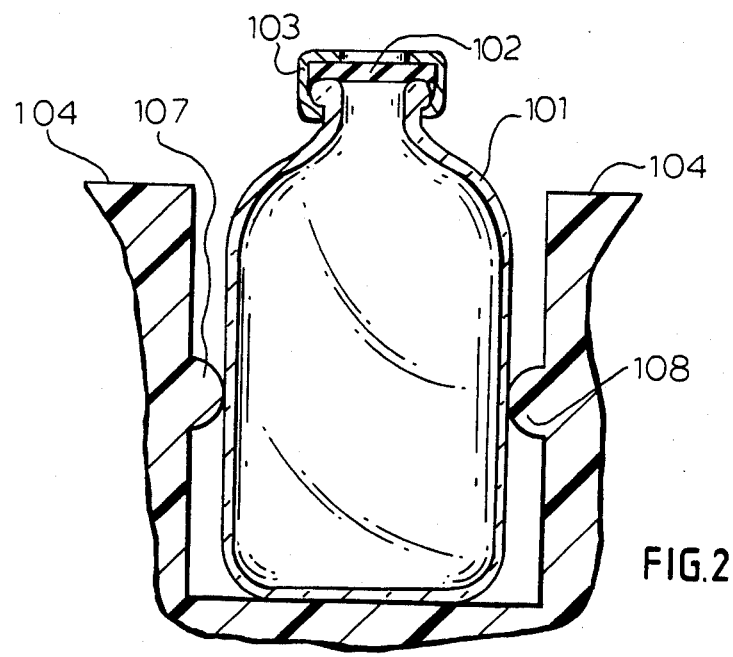
FIG. 2 is a cross section taken through A—A' of FIG. 1.
Figure 3:
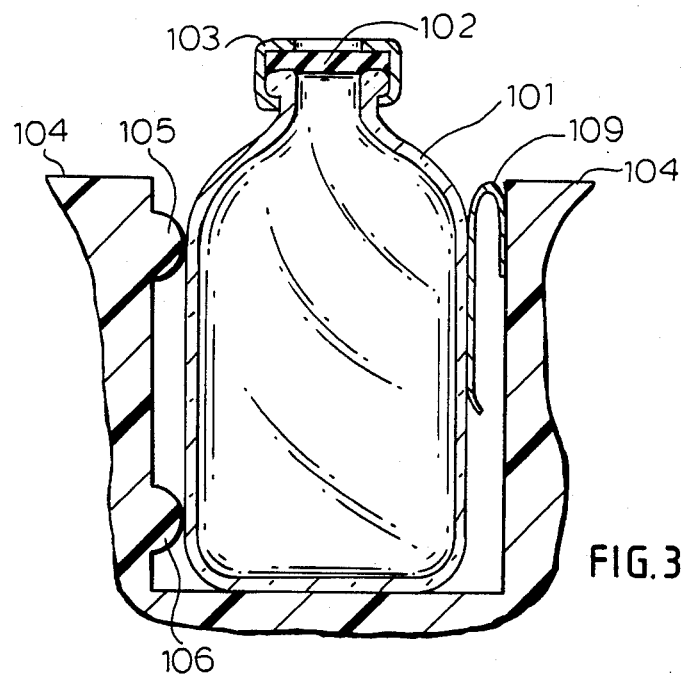
FIG. 3 is a cross sectional view taken through section B—B' of FIG. 1.

Referring now to the drawings, FIG. 1 shows a preferred embodiment of an arrangement for locating the vial in a unique orientation and in a predetermined position with respect to a plurality of needles which penetrate the septum of the vial at periodic intervals. The vial, 101, has a straight sided body whose cross section has the shape of an isoceles trapezoid with rounded corners. The vial, 101, has a circular finish and a circular septum, 102, and circular seal, 103. The vial, 101, fits into the vial carrier, 104, which is a well in a rotating turntable, or other device for bringing vials successively into position for penetration by the needles. The vial carrier, 104, is provided with bosses, 105, 106, 107, 108, against which the vial, 101, is pressed by a spring, 109, attached permanently to the vial carrier, 104. The bosses, 105, 106, 107 and 108 and the spring, 109, together constrain the vial, 101, to prevent rocking or rotation of the vial, 101, within the vial carrier.

As shown in FIG. 1, the bosses, 105, 106, 107 and 108 and the sidewalls of the vial, in combination, provide a plurality of contact points and a locating surface. A spring, 109, urges the vial into contact with the bosses, 105, 106, 107 and 108 and establishes the predetermined location of the vial within the vial carrier.

Figure 4:
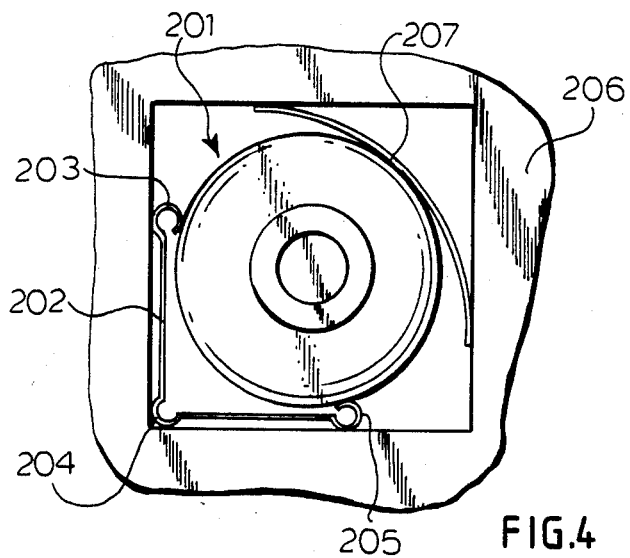
FIG. 4 is a top plan view of a further embodiment of the vial and vial carrier in accordance with the present invention.

If desired, circular vials may be prevented from rotating in a system in accordance with the invention by bonding a locating object to the exterior of the body of the vial or by inserting the vial into a non-circular sleeve. The assembly of the vial and the locating object is then inserted into a vial carrier. FIG. 4 shows an embodiment utilizing a circular vial. A circular vial, 201, has bonded to its side an attachment, 202. This attachment has contact projections 203, 204 and 205 which function in a manner similar to the bosses on the vial carrier 104, as shown in FIG. 1. The bonded assembly of the vial 201 and the attachment, 202, are forced into one corner of the well in the vial carrier, 206, by the action of a spring, 207.

The projections 203, 204 and 205 provide contact points which function in combination with the sidewall of the vial carrier as a locating surface. The spring 207 urges the vial into a predetermined location in respect to penetrating needles.

A further modification of the arrangement shown in FIG. 4 would be to make the attachment a sleeve which would extend around the vial. This embodiment has the advantage of permitting a greater extent of contact between the attachment and the vial. The sleeve could be attached to the vial or could be of a nature to permit a friction fit between the sleeve and the vial.

Heretofore, the use of either the sidewall of the vial carrier or the sidewall of the vial has been described as providing a locating surface with respect to contact points. If the septum is attached to a vial using a metal seal crimped around the septum and the lip of the vial, the vial is usually provided with a circular finish for ease in crimping the seal. Other means of attaching the septum permit the finish of the vial to be non-circular. Such other attaching means would include crimping a seal to a non-circular finish, holding the septum with a screw cap having a non-circular exterior, attaching, by bonding or by friction-fit, a non-circular object over a circular seal or a circular screw cap, and molding a non-circular finish around the septum so that no seal is required.

The non-circular finish can then be used as a locating surface. Contact points would then be provided which extend from the wall of the vial carrier. Alternatively, a test head can be provided in the instrument which has a cross sectional opening conforming to the non-circular top portion or finish. The vial can then be located for positioning needles and restrained against rotation by the matching non-circular test head which would capture the vial for location.

In order to ascertain that the needles will always re-enter the openings in the septum made on the first test, the needle points must continue to occupy their original locations relative to the vial. Under some circumstances the needles must be changed between tests and the desired accuracy for re-entry of the needle points into the original locations would require the use of needle guides or the use of a locating device to position the needles in the same positions as the original needles.

In some circumstances, the use of needle guides may be undesirable but there may still be a need to change needles between tests. Repeated entry of the needles to the same two spots on the septum would not then be assured. The distribution of septum damage can be made uniform, however, by stepping the needles through sequential positions.

One means of obtaining the sequential positions, which is well adapted for use with a circular septum, is to employ angular indexing of the needles. To accomplish this the vial, in its predetermined position, is used in combination with a mechanism or system for changing the angle between the predetermined position of the vial and the line joining the two needles. Such indexing would be carried out each time a new needle set is installed. The required indexing of the needles may be obtained either; (1) by holding the needles in a carrier which is indexed into successive angular positions in the test head, or (2) by providing serially-marked needle carriers which are installed in the test head in order and which contain the needles mounted in a sequence of angular positions.

The two needles may be located so that they penetrate the septum at points equidistant from its center. In this case, a number N of distinct locations may be obtained by each time indexing the needles through an angle of 180/N degrees.

If the two needles are located at different distances from the center of the septum, a number P of distinct locations may be obtained by each time indexing the needles through an angle of 360/P degrees. This latter scheme is not advantageous unless the number of pairs of locations required is greater than six.

Although angular indexing of the needles is usually the most convenient form of sequential location for use with a circular septum, other sequences can be used, subject only to the condition that the sequence must maintain sufficient space between the puncture locations so that the areas of possible septum damage do not overlap.

As a particular example, a system in which vials having a standard 20 mm circular finish are tested on an instrument using needle pairs which are to be changed daily. New vials arrive daily and each vial is to be tested for five days, using five different needle pairs. On some days, a vial is tested more than once, but those repeated tests use identically the same needle pair. The vials have the cross sectional shape of an isosceles trapezoid and are located as described in FIG. 1. The two needle locations for each penetration are equidistant from the center of the septum which seals the vials. The instrument is provided with five sets of serially numbered needle sets. Each set locates the two needles at an angle of 36 degrees from their location in the previous set. The daily replacement of needle sets uses the set bearing the next higher number, up to set number 5, after which the sequence is repeated.

If, in this example, the centers of nominal needle locations form a circle of radius R, the distance between adjacent nominal locations is $$d = 2R \sin 18°$$

If the two needles are located 0.260 inch apart, R is equal to 0.130 inch. In this case, d equals 0.080 inch. This is sufficient separation between adjacent punctures to avoid septum damage.

What is claimed is:

1. A system for locating a vial comprising
   a. a vial carrier comprising a well,
   b. a vial having a cross sectional shape which permits insertion in said vial carrier, said vial having a body portion, a finish, an opening in said finish and a penetrable septum disposed in said opening,
   c. said septum being penetrated by at least one needle at periodic intervals, and
   d. locating means within said vial carrier for establishing a predetermined location for said vial in relation to said needle, said locating means fixing the location of the vial within the well while placed therein, said locating means including a plurality of contact points and urging means for establishing contact between said contact points and a locating surface, said urging means pressing substantially on one side of said vial, which side is substantially opposite said locating means.

2. A system in accordance with claim 1 wherein said septum is penetrated by a plurality of needles at periodic intervals.

3. A system in accordance with claim 1 wherein said vial carrier is provided by a rotating turntable having a plurality of wells.

4. A system in accordance with claim 1 wherein said body portion of said vial has circular cross sectional shape.

5. A system in accordance with claim 4 wherein said contact points are part of an attachment affixed to said circular body portion of said vial.

6. A system in accordance with claim 4 wherein said contact points are located on a non-circular sleeve.

7. A system in accordance with claim 6 wherein said sleeve is attached to said vial.

8. A system in accordance with claim 6 wherein said sleeve is friction fit to said vial.

9. A system in accordance with claim 1 wherein said body portion of said vial has non-circular cross sectional shape.

10. A system in accordance with claim 9 wherein said non-circular shape is substantially that of a polygon.

11. A system in accordance with claim 10 wherein said polygon is a triangle.

12. A system in accordance with claim 11 wherein said triangle is equilateral.

13. A system in accordance with claim 11 wherein said triangle is isosceles.

14. A system in accordance with claim 10 wherein said polygon is a quadrilateral.

15. A system in accordance with claim 14 wherein said quadrilateral is an isosceles trapezoid.

16. A system in accordance with claim 1 wherein said finish is circular.

17. A system in accordance with claim 1 wherein said finish is made non-circular.

18. A system in accordance with claim 17 wherein said locating surface is positioned on said non-circular vial finish.

19. A system in accordance with claim 17 wherein said septum is restrained in said opening with a screw cap having a non-circular exterior.

20. A system in accordance with claim 17 wherein said septum is restrained by friction-fitting a non-circular object over said non-circular vial finish.

21. A system in accordance with claim 1 wherein said body portion of said vial and said finish of said vial have different cross sectional shapes.

22. A system in accordance with claim 1 wherein said locating surface is a wall of said well of said vial carrier.

23. A system in accordance with claim 1 wherein said locating surface is a wall of said body portion of said vial.

24. A system in accordance with claim 23 wherein said contact points are attached to said wall.

25. A system in accordance with claim 1 wherein said contact points are a plurality of bosses.

26. A system in accordance with claim 1 wherein said urging means is affixed to said vial carrier.

27. A system in accordance with claim 26 wherein said urging means is a spring.

28. A system in accordance with claim 26 wherein said urging means is elastomeric.

29. A system in accordance with claim 1 wherein said septum is restrained in said opening with a crimped metal seal.

30. A system in accordance with claim 1 wherein said needle is positioned with needle guides.

* * * * *